United States Patent [19]

Parmer

[11] 4,088,753
[45] May 9, 1978

[54] METHOD OF OBTAINING A SPLENIC COMPOSITION WHICH INHIBITS PLATELET FUNCTION AND SAID COMPOSITION

[76] Inventor: Laurence Pierpont Parmer, Lakewood, N.J.

[21] Appl. No.: 688,224

[22] Filed: May 20, 1976

Related U.S. Application Data

[63] Continuation-in-part of Ser. No. 568,593, Apr. 16, 1975, abandoned.

[51] Int. Cl.² ............................................ A61K 35/28
[52] U.S. Cl. .................................................... 424/95
[58] Field of Search ......................................... 424/95

[56] References Cited

U.S. PATENT DOCUMENTS

| | | | |
|---|---|---|---|
| 2,616,826 | 11/1952 | Moolten | 424/95 |
| 2,662,047 | 12/1953 | Amozurrutia | 424/95 |
| 2,987,443 | 6/1961 | Littman et al. | 424/95 |

OTHER PUBLICATIONS

Steiman et al.–Chem. Abst. vol. 75, (1971), p. 116,538j.

*Primary Examiner*—Sam Rosen

[57] ABSTRACT

A process is provided for extracting and isolating a material from a spleen which is capable of inhibiting platelet function. It has been found that such material is capable of lowering platelet count or fibrinogen concentration or both. The process includes the steps of subjecting the spleen to a polar solvent and subjecting the filtrate to a chromatography process to obtain certain $R_f$ values.

12 Claims, 11 Drawing Figures

▲ = 4 mg TLC 2
⬢ = 4 mg TLC 2
● = 8 mg TLC 2

TIME (HOURS) POST S.C. INJECTION

FIG. 4

EFFECTS OF EQUAL
AMOUNTS OF TLC 2
INJECTED INTO 2 RABBITS

TIME (HOURS) POST S.C. INJECTION

METHOD OF OBTAINING A SPLENIC COMPOSITION WHICH INHIBITS PLATELET FUNCTION AND SAID COMPOSITION

This is a continuation-in-part application of application Ser. No. 568,593, filed Apr. 16, 1975, now abandoned.

SUMMARY OF THE INVENTION

This invention is concerned with novel procedures for isolating and extracting novel compounds from the mammalian spleen which significantly reduce platelet counts, markedly increase bleeding times, reduce or inhibit ADP induced platelet aggregation in vivo and in vitro, decrease clottable plasma fibrinogen concentration, prevent endotoxin produced coagulation, and most importantly prevent experimental thrombosis.

The ability of these compounds to decrease platelet counts is demonstrated in laboratory animals such as guinea pigs, rabbits and dogs. The magnitude and duration of the decrease depends upon the material employed, dosage administered and species of test animal utilized. In rabbits and guinea pigs, decreases of 20–50% of baseline counts lasting from a few hours to two weeks were observed. With dogs, 20–50% changes with relatively small doses of these compounds were found.

The ability of these compounds to inhibit platelet function is demonstrated by the increased bleeding times of recipient mice, inhibition of ADP mediated platelet aggregation in vivo and in vitro, and the ability to prevent experimental thrombosis in rabbits. Another example of inhibition of platelet function was found in the ability of these extracts to protect mice from disseminated intravascular coagulation (DIC) resulting from the injection of lethal doses of bacterial endotoxins. Mice protected with these extracts have 68% survivals whereas unprotected mice have a survival of but 20%.

In bleeding time determinations, a mouse mesentery vein was punctured and the time for bleeding to stop recorded. In treated mice the bleeding times increased markedly to 250+% compared to saline injected controls.

In experimental thrombosis experiments, a plastic tube was inserted into the great vessels of animals to simulate a damaged atherosclerotic plague, which became the nidus for thrombus formation. Animals receiving the compounds of this invention survived the experiment, whereas unprotected animals all succumbed to major thrombi.

ADP induced platelet aggregation experiments revealed the inhibitory effect of inventive compounds in vitro and in vivo. When administered into dogs or rabbits, the compounds inhibited aggregation to 50% of the baseline values. When added to human or dog platelet rich plasma inhibitions up to 40+% were obtained with no prior incubation of the materials with the cells.

The mechanisms by which the inhibition of platelet function occur can be numerous. Firstly, these compounds may attach themselves to the platelet membrane and thus protect the reactive sites which prevents the platelet from becoming activated. Secondly, platelet aggregation decreases with decreasing platelet counts and since the inventive compound produces this effect in vivo, less ADP and fibrinogen (from platelets) are released to promote further aggregation. Thirdly, since less clottable fibrinogen is available, platelet aggregates cannot be formed or stabilized due to the inability of the aggregate to form a fibrin network. It is known that platelets aggregate in proportion to the amount of fibrinogen present. Fourthly, since this material produces an uptake of $^{51}Cr$ tagged platelets in the spleen, lungs and liver, organs rich in reticuloendothelial tissue, the effect may be mediated through a stimulatory effect on the reticuloendothelial system. Finally numerous other mechanisms are possible, including the removal of other factors necessary for coagulation or platelet function.

The administration of the novel compounds into dogs disclosed a decrease in the quantity of clottable fibrinogen in the plasma. However, the magnitude of such decrease cannot always be related to the change in platelet count. Decreases of from 20 to 60% of baseline values have been observed with no detection of fibrin split products. This may indicate that either the fibrinogen is complexed in such a manner as to not allow its participation in the clotting sequence or it may be sequestered by some organ. Such a decrease in clottable fibrinogen may in part explain the increases in bleeding times, inhibition of ADP induced aggregation and the prevention of experimental thrombosis.

Accordingly, it is an object of this invention to provide a method of extracting and isolating a material from a spleen which, in turn, is capable of inhibiting platelet function and includes the lowering of animal platelet counts or fibrinogen concentration or both.

Broadly, the process includes the steps of subjecting the spleen to a polar solvent having a high dielectric constant preferably of at least 20 whereupon the resultant polar solvent filtrate is subjected to a chromatography process for separating the desired material therefrom having an $R_f$ value ranging from about 0 to 0.73.

DESCRIPTION OF THE PREFERRED EMBODIMENT(S)

In accordance with a preferred embodiment of the invention, seven bovine spleens, totalling approximately 6 kilograms, were removed from freshly killed animals and immediately submerged in 15 liters of a liquid solvent having a high dielectric constant of at least 20, such as acetone, at room temperature. While reference is made to bovine spleens, it should be noted that canine spleens or those of other species may be employed. The spleens were removed from the acetone, sliced and ground into fine particles. The ground spleen particles then were returned to the original acetone, stirred and set aside for approximately four days to allow the extraction to proceed. It was found that the aforesaid set aside period can range from about two to thirty days.

Preferably three liters of the acetone were removed at one time and filtered, the solvent being removed by a conventional Buchler rotary evaporator. During the solvent removal, a vacuum was applied to the system and the temperature of the extract was maintained between 40° and 50° C, preferably 45° C. When a moist paste remained, 2 liters of benzene was added thereto and the entire contents stirred for about 30 minutes. The material was filtered and the benzene soluble filtrate was concentrated by allowing the benzene to evaporate under a fan forced draft. Ether, chloroform, dichloromethane and other solvents could also be employed. Subsequently, silica gel thin-layer (TLC) or silica column chromatography (CC) was then employed to further purify the mixture. Sephadex LH-20, Florasil, alumina, ion exchange or other absorbants, as well as electrophoresis and gas chromatography could likewise be used. It is understood that the term chromatography, as used herein, is defined to cover the aforesaid.

EXAMPLE I

In a typical thin layer chromotography example, the benzene soluble material was streaked on a 20cm × 20cm glass backed Brinkman silplate, silica gel F-254 having an absorbant thickness of 250 or 500 microns, without any activation of the plate by heat. If necessary, additional benzene may be utilized to dissolve all the materials. After repeated applications of the material to the silica, the solvent was evaporated by conventional means and the plate was placed in a standard Brinkman developing tank containing one saturation pad and eluting solvent, benzene. The solvent was allowed to migrate at least 7 cm before the plate was removed from the tank, whereupon the solvent was then evaporated from the plate. The plate with the resultant material thereon was then exposed to ordinary light and an ultraviolet lamp (U.V.) having a wave length of 254 millimicrons to observe the material (fractions) which emanated from the point of origin on the plate. Such fractions hereinafter are referred to as TLC 1, TLC 2 TLC 3. Initially, when the plate was held up to the light, a large opaque area was observed, and a brownish material remained at the origin. In general, the $R_f$ values (distance fraction moves divided by distance solvent migrates) for the fractions are as follows: the U.V. visible fraction TLC 1 is from 0.72 to 0.53; the opaque fraction TLC 2 is from 0.53 to 0.33; and, fraction TLC 3, the brownish material, remained at the origin. The large range in $R_f$ values is believed attributable to the irregular shapes of the bands and the relatively large amount of material applied to the plate.

Under the above conditions the dyes butter yellow, sudan red 6 and indophenol blue had $R_f$ values of 0.43, 0.17 and 0.09 respectively. If smaller quantities of crude extract are applied to the thin-layer plate then the $R_f$ values of the various fractions are as follows: TLC 1 approximately 0.6; TLC 2 approximately 0.4 through 0.2 (for convenience TLC 2 is the material with $R_f$ values between that of the dyes butter yellow and sudan red 6. This fraction has two major components, a faster moving TLC 2A and a slower moving TLC 2B; and TLC 3, the materials remaining at the origin.

The desired fractions then were scraped from the glass backing and the silica absorbing them was extracted with benzene. The fractions then were centrifuged for about 5 minutes at about 2500 r.p.m. to remove the silica. The benzene was decanted followed by the addition of acetone and stirring for about 5 minutes. Finally, the material again was centrifuged and the acetone decanted. The benzene and acetone solvents were combined and then removed in a stream of air or nitrogen leaving behind a low melting point solid. (M.P. < 70) or an oil. The dried fractions TLC 1, 2 and 3 were then stored in a freezer at a temperature of about −20° C or below. Upon rechromatography under identical conditions, the active materials TLC 1, TLC 2 and TLC 3 yielded the spot with the $R_f$ value collected, plus additional spots with different $R_f$ values ($I_2$ visualization).

EXAMPLE II

In a typical glass column chromatography example, sixty grams of Mallinckrodt silicic acid (2847) was suspended in petroleum ether and the slurry poured into a glass chromatography column (2.75 × 40 cm) with a fritted glass disc. The packed column had a final height of 24.5 cm. The benzene extract was dissolved in benzene and added to the column, and after adsorption was eluted with benzene. The opaque material could be seen coming down the column which was collected and designated fraction CC 1. A yellowish band next was observed in the column which was collected and designated fraction CC 2. The succeeding portion of the solution in the column was collected until a brownish tar portion remained, said succeeding collected portion being designated fraction CC 3 and the brownish tar solution being designated CC 4. Methanol was utilized as the eluting solution for CC 3 and CC 4. The solvents were evaporated off from the aforesaid eluted fractions under a stream of nitrogen and fractions CC1 - CC4 were stored in a freezer. If desired, the eluted fractions could be purified by subjecting same to chromatography in a similar manner to that heretofore described.

EXAMPLE III

Spleens from two female canines weighing a total of 170 grams were cut and ground with 850 ml. (5 volumes) of acetone. The mixture was placed in a five liter flask and placed on a steam bath to reflex for 30 minutes. The material was filtered hot to a temperature of about 57° C, the acetone evaporated, and the resultant material stored in a freezer, similar to that as hereinbefore described. After the acetone was removed, the benzene soluble fractions were obtained in a manner to that previously described. Further purification was achieved by thin layer chromatography, as previously described. It should be noted that progressively longer refluxing produces a lower yield of active materials.

EXAMPLE IV

A similar procedure was employed to that carried out in Example III, except for the refluxing step. In lieu thereof, the mixture was permitted to stand at 45° C for a period of 18 hours, and similar type fractions to those obtained in Example III were recovered.

EXAMPLE V

A similar procedure was employed to that carried out in Examples III and IV except that the acetone filtrate was subjected to a chromatography process directly. Acetone was used to isolate the desired materials from the silica. If desired, fractional crystallization of this acetone solution could be carried out with the more soluble material, usually more active.

EXAMPLE VI

A similar procedure was employed to that carried out in Example V except that a lethal dose of E. Coli endotoxin was administered to the dog, and three hours later the dog was sacrificed and the spleen treated as in Example V. It was found that the fractions recovered in this experiment were at least as potent than those previously described, as set forth in more detail hereinafter.

TESTS OF RECOVERED FRACTIONS

Each of the isolated fractions, that is TLC 1, TLC 3 and CC 1 - CC 4, recovered from Examples I and II, respectively, were weighed, dissolved in ether, filtered and added to injection bottles containing sterile saline to form a suspension. The ether was removed under vacuum and each of the resulting suspensions were administered to test animals. The suspensions may be administered subcutaneously, intramuscularly, intraperitonially, orally, or intravenously; however, unless stated otherwise is is to be understood that the injections were subcutaneous.

The standard animals used to test the effects of the suspended fractions for platelet counts were rabbits (6 Kg) and guinea pigs (1 Kg). These animals were tested at least twice weekly for at least thirty days, before the administration of these fractions, to determine their normal platelet counts (large and small platelets) total white counts (TWC) and differential white counts (DWC). The Unoppette method was used for platelet counts, Wrights' stain for differential counts, and a Coulter Counter for total white counts. No significant changes were observed for either the TWC or the DWC prior to testing.

Blood was drawn from the marginal ear vein of each animal before injection and serially on a daily basis after injection, for a period of two weeks. Typical effects on injected fractions on platelet counts are shown in FIGS. 1 to 5. Baseline counts did not differ by more than ± 50,000 platelets/cc from the value at time zero on graphs.

Figure 1:
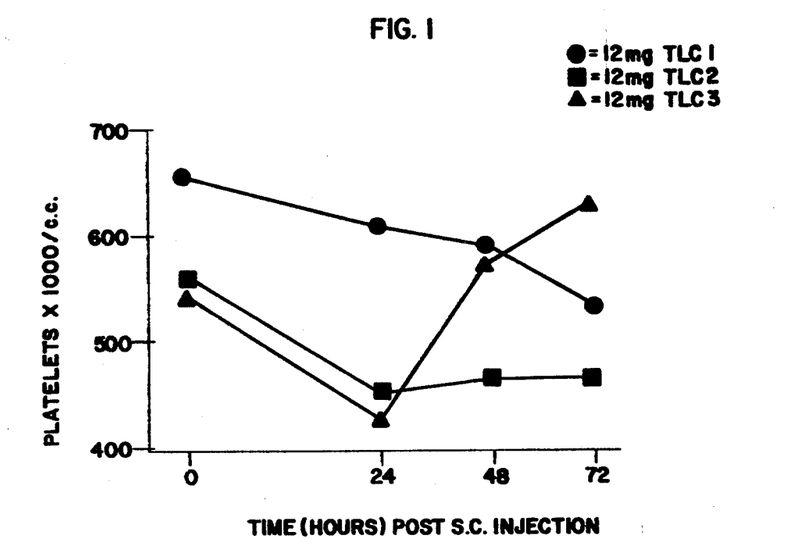

From FIG. 1, it can be seen that all fractions have a platelet reducing (thrombocytopenic) effect on rabbits. The magnitude of the changes is average for the injection of about 20 mgs. of the active fractions isolated by thin-layer chromatography.

Figure 2:
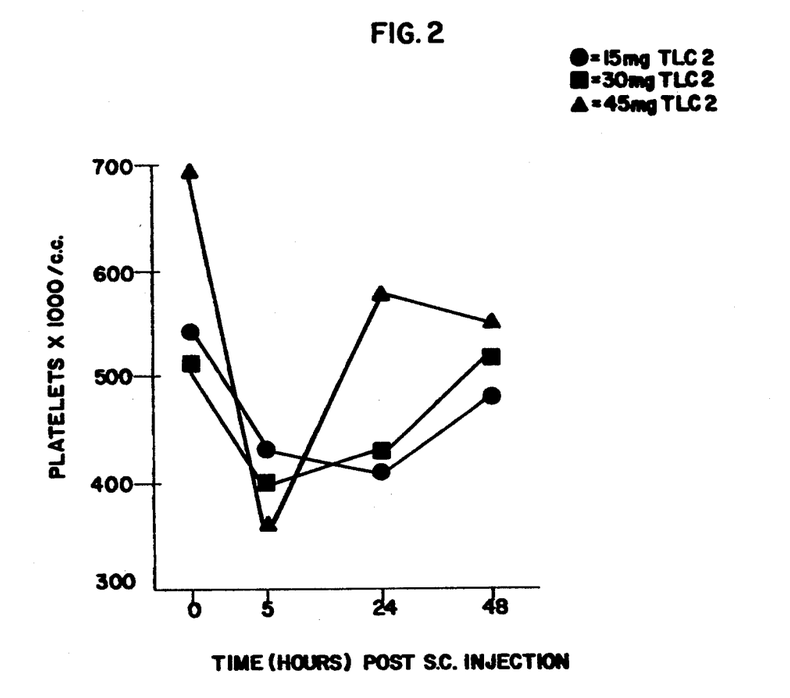

FIG. 2 depicts the variation in effects when varying amounts of TLC 2 are injected into female rabbits of the same weight. It can be seen that the largest dose causes the greatest decrease in platelets after five hours but that after 24 hours the percentage change is similar in all cases. It is noted that the thrombocytopenic effect lasted 48 hours.

Figure 3:
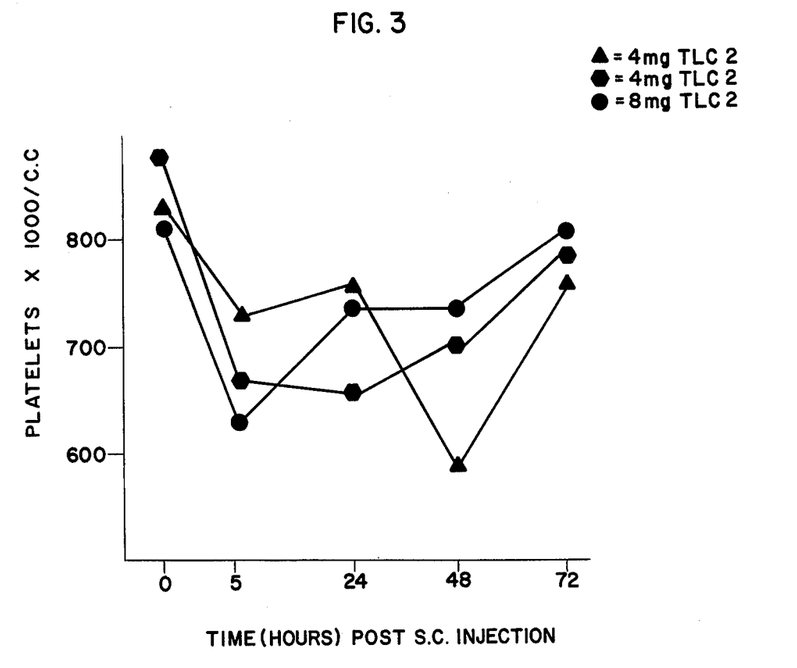

In FIG. 3, there is shown the effect of varying doses of TLC 2 in guinea pigs. It is noted that the thrombocytopenic effect lasted 72 hours.

Figure 4:
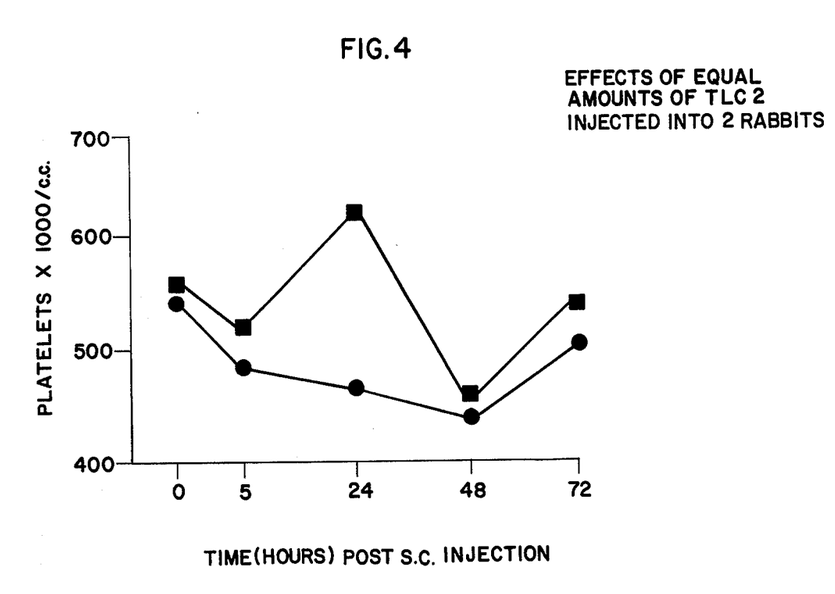

FIG. 4 depicts the employment of TLC 2 isolated from canine spleens. In this instance both rabbits received the same dose of material. It can be seen that the platelet count in one rabbit increased from the five to twenty-four hour period and then decreased from the twenty-four to forty-eight hour period. While this is a rare occurrence, it tends to show that biological individuality of the species has much to do with the magnitude of the effect.

Figure 5:
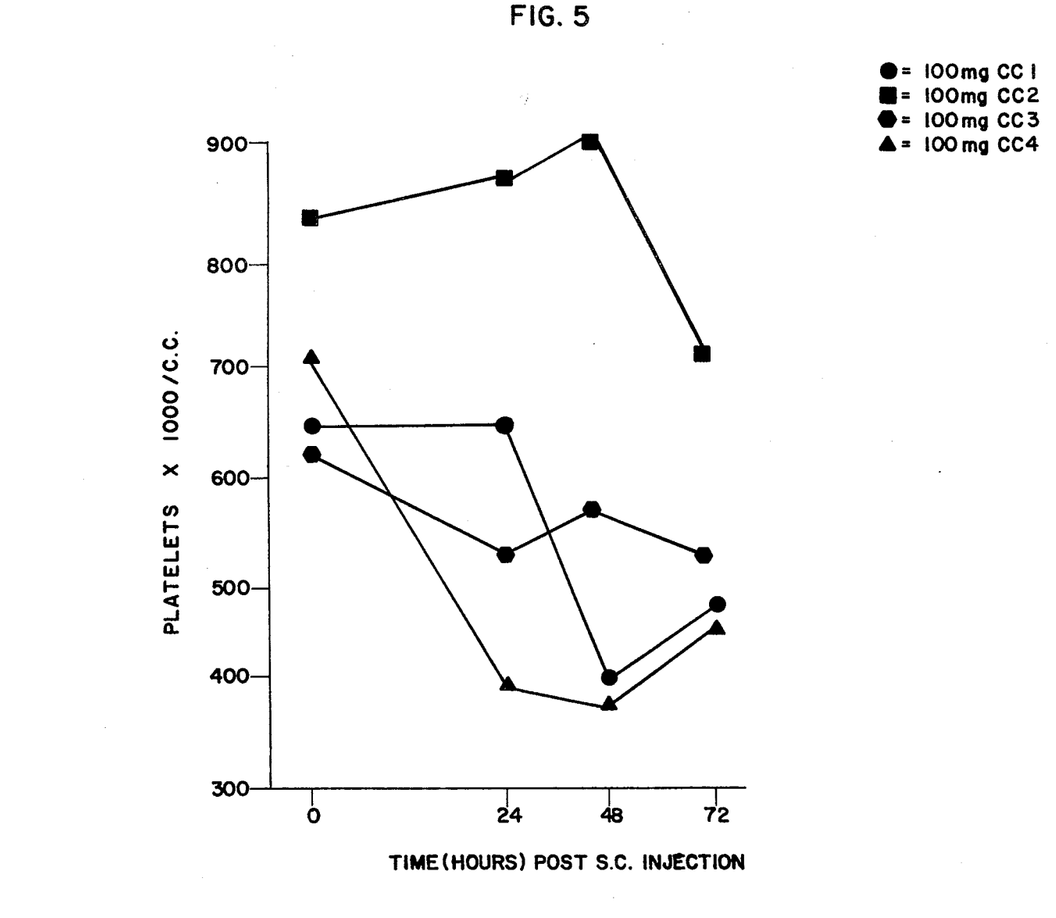

FIG. 5 shows the results of the various fractions isolated by column chromatography. The magnitude of the effects are greater since 100 mg. of material were injected in each rabbit as opposed to the smaller dosage administered to the animals whose effects are shown in FIGS. 1–4. Saline injections were found to have no effect on platelet counts while a very few isolated fractions increase the platelet count.

In general, it was found that many fractions, when freshly prepared and administered to the animals, resulted in a lowering of the platelet counts. Further when a chromatographed fraction is stored for about three weeks, it decomposes and loses its activity. Upon the injection of a decomposed fraction to rabbits and dogs, it was observed that, in fact, the platelet counts were increased. This was particularly true of fractions TLC 1, TLC 2, CC 1, CC 2 and CC 3. Fractions CC 4 and TLC 3, upon storage, appear to lose their ability to either lower or raise platelet counts.

The possibility exists that the active principle may be incorporated in all the active fractions, though the matrix of inert materials may be different. It could also be that the effects of the active fractions are similar but not identical in action.

It is of considerable importance to recognize that the test animals were in excellent health and significant effects were observed. It may likely be that injection of these fractions to patients of high thrombotic risk will show more profound changes in hematology, platelet function and coagulation profiles.

BLEEDING TIMES (BT)

It is well known that bleeding time is a prime test for platelet function and as utilized herein is a function of the quality of the platelet, and to a lesser extenet the quantity. The mouse mesentery method for bleeding times described by R. G. Herrmann, J. D. Frank and D. L. Marlett, Proc. Soc. Expl. Biol. Med. 128 960 (1968) was employed. Each determination of a bleeding time was done on a minimum of five mice. Increases in bleeding time are apparent (Table I), three hours after intraperitonial injection, and remained elevated for twenty-four hours post dosing with prolonged B.T. still observed forty-eight hours post dosing. In general, less than 0.2 mg. injected into 20 gm. mice will increase the B.T. significantly within twenty-four hours after dosing. The injected fractions show the increase in bleeding time which, in turn, presupposes a lesser degree of aggregation of platelets and, accordingly, decreases the chance of the formation of a clot:

TABLE I

| | BLEEDING TIMES (BT) | | |
|---|---|---|---|
| Fraction | Hours Post Dosing | B.T. (Min) | % Increase Over Saline Controls |
| TLC 2 | 24 | 1.20 | 240 |
| TLC 1 | 24 | 1.20 | 250 |
| TLC 2 | 3 | 1.24 | 150 |
| TLC 3 | 3 | 1.00 | 127 |
| CC 1 | 24 | 0.92 | 185 |
| CC 1 | 4 | 1.50 | 300 |
| CC 1 | 48 | 1.00 | 100 |
| Saline (control) | — | 0.50 | — |

In addition to the increase in B.T., it was observed that when the veins of the treated mice were pierced, the blood gushed out of the wound, whereas use of the saline controls caused the blood to just "ooze" out upon piercing.

The quantity of active fractions which fractions which are administered may have a profound effect on the B.T. The optimum doses are usually between 3 and 16 mg/kg body weight. Other doses may give rise to no change in B.T. or even a decrease if very large amounts are administered.

In some instances, it was found that fractions which had no significant effect on lowering platelet count in rabbits or guinea pigs still had the ability to increase bleeding times. This probably was due to either (a) a qualitative change in the platelet or its function or (b) a decrease in the amount of effective fibrinogen to prevent platelet aggregation and formation of a clot or (c) both.

ADP INDUCED PLATELET AGGREGATION

Generally, the most widely used technique employed for testing antithrombitic drugs is ADP induced platelet aggregation. Human PRP (platelet rich plasma) from coronary prone individuals, as well as from cancer patients, have been tested in vitro with these extracts to measure the percent decrease in platelet aggregation relative to saline. The extracts are prepared as previously described and are suspended in saline, centrifuged and the solution added to the platelet rich plasmas. One tenth cc saline (controls) or extract in saline, 0.3 cc PRP and 0.04 cc (20 microgram/cc) ADP is added. Aggregation is followed for two or three minutes with a Chrono-Log Platelet Aggregometer. Varying dilution can be made of these extract solutions with saline if desired. the results are as follows:

| Type Human PRP | Number of Determinations | % Aggregation Saline Controls | % Aggregation Extract | % Inhibition |
|---|---|---|---|---|
| coronary prone | 25 | 69.2 | 58.1 | 11.2 |
| cancer patients | 6 | 69.2 | 53.6 | 15.6 |

The rationale of using the PRPs of coronary prone individuals and cancer patients for the testing of these extracts is concerned with the fact that a much higher sensitivity is found in these individuals' platelets to ADP, in particular, and aggregation in general to less coronary prone and cancer free individuals.

Again it must be emphasized that the inhibition of ADP induced aggregation by these extracts is a function of the individuals' PRP and concentration of "active" material in the extract. If the extract remains in saline, its ability to inhibit aggregation diminishes with time and, in fact, after a few days produces a greater percentage aggregation than that of the saline controls. This experimental observation confirms the labile nature of the active materials in these fractions.

IN-VIVO. Blood (control) was drawn from a dog and 1 ml 3.8% sodium citrate was added to each 9 ml of blood, to obtain a control PRP. Two mgs. per kg per body weight of each fraction TLC1 and TLC2 were were injected into the dog and blood again was drawn 2 to 3 hours later, the PRP being obtained in an identical manner. It was found that the ADP induced aggregation was inhibited about 50% (platelet count 122,000/c.c.) from that of the control PRP (platelet count 325,000/c.c.) Upon repeated expeated experiments, it was observed that the inhibition of aggregation was not necessarily proportional to the platelet count decrease.

THROMBOSIS TESTS

Thrombosis tests were performed to further illustrate the effect of the recovered fractions on blood platelets. Female protected rabbits, hereinafter referred to as Group A, each were injected with a platelet reducing fraction, while a like number of unprotected female rabbits, hereinafter referred to as Group B, were used as a control.

Initially, 10cc of saline was introduced into a 30cc bottle placed under vacuum for each fraction. Each bottle with the saline therein was sterilized, whereupon fractions TLC 1, TLC 2 and TLC 3 (approximately 10 mg/kg) each were dissolved in ether and then introduced into its respective bottle. Each bottle was shaken and, under vacuum, the ether was drawn from the solution.

To each of the rabbits of Group A, 10 cc of the active material was injected intramuscularly. To each of the control rabbits of Group B, 10cc of saline alone was injected intramuscularly. It should be noted that there were 3 Group A and 3 Group B, since the test employed for each Group A and B involved the use of TLC 1, TLC 2 and TLC 3, respectively. Twenty-four hours later, an operation was performed on each of the rabbits of Group A and Group B, whereby polyethylene tubing, 2-3 cm in length, was introduced into the abdominal aorta of two rabbits of Group A and two rabbits of Group B, and 2.3 cm of similar tubing was introduced into the inferior vena cava of the other two rabbits of Group A and Group B. Each of the aforesaid operations were performed according to the Freidman technique.

Within 35 hours after the operations, all of the unprotected rabbits of Group B were dead, while all of the rabbits of Group A were alive and normal. Upon an examination of the Group B rabbits, it was learned that an intravascular thrombosis was produced in each rabbit, the thrombis extending within the tubing and extending axially approximately 2 cm on each end.

After 3 days, the protected rabbits of Group A in each test, were destroyed. Upon an examination of these rabbits, no signs of any thrombus, clot or coagulation of blood in any part of the vascular system was found. It was concluded that the administration of each of the platelet reducing fractions in the three tests sufficiently controlled the blood platelets to prevent any intravascular thrombosis, which normally would have resulted due to the introduction of a foreign substance, such as polyethylene tubing, into the vascular system.

EFFECT OF FRACTIONS ON COAGULATION

It is well known in the art that there are several stages in clinical parameters which measured coagulation, including activated partial thromboplastin time (APTT), prothrombin time (PT), thrombin time (TT) where fibrin forms, and clottable fibrinogen concentration. Accordingly, tests employing the fractions were conducted with human plasma and animal plasma.

To human plasma, in vitro, fractions TLC 2 and TLC 3, having a final concentration of 0.05 mg/ml in the plasma, were introduced. It was found that the APTT was increased 15% and 5% respectively against a saline (human plasma) control, while the fibrinogen was markedly reduced by up to 30% in each.

Figure 6:
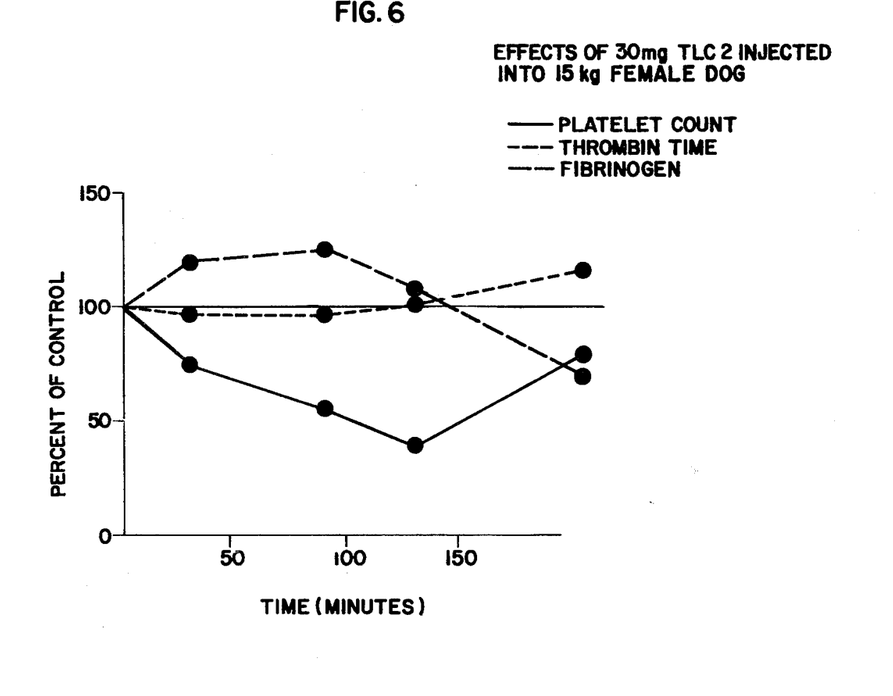
Figure 7:
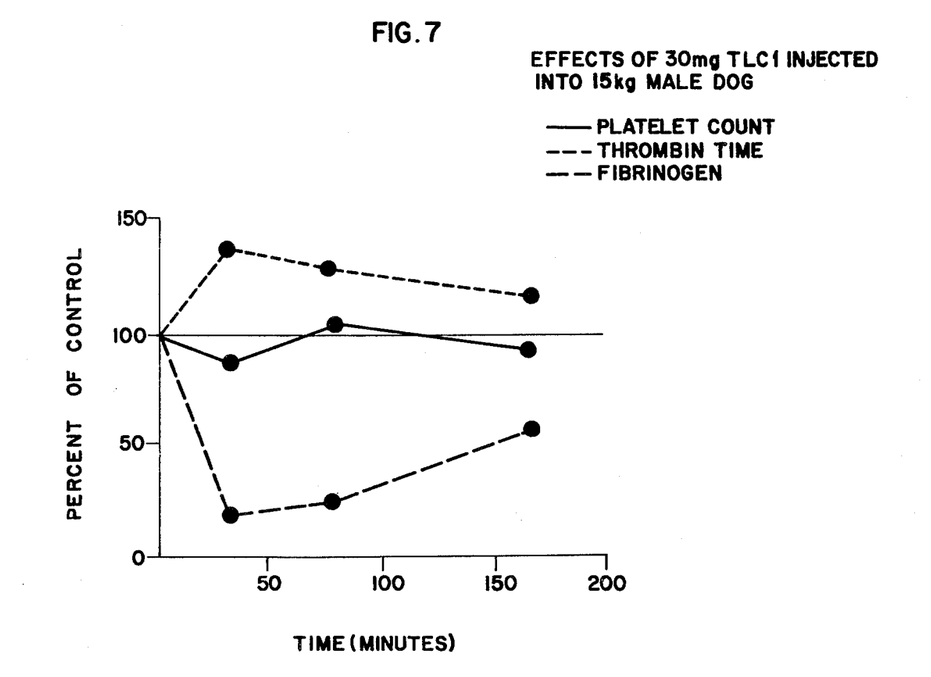

Upon the intraperitonial injection of 30 mgs of TLC 2 to female dogs weighing approximately 15 kgs, significant changes occured in the coagulation profile of the plasma, as can be seen from FIG. 6. After three hours, a 15% increase in T.T., and 30% reduction in clottable fibrinogen concentration occured. Similar results were obtained with other dogs except for the times at which the platelet count and fibrinogen concentrations decreased and the T.T. increased. As seen in FIG. 7, some dogs disclosed an 80% reduction in fibrinogen and a 40% increase in T.T. at 30 minutes post intraperitonial injection.

Figure 8:
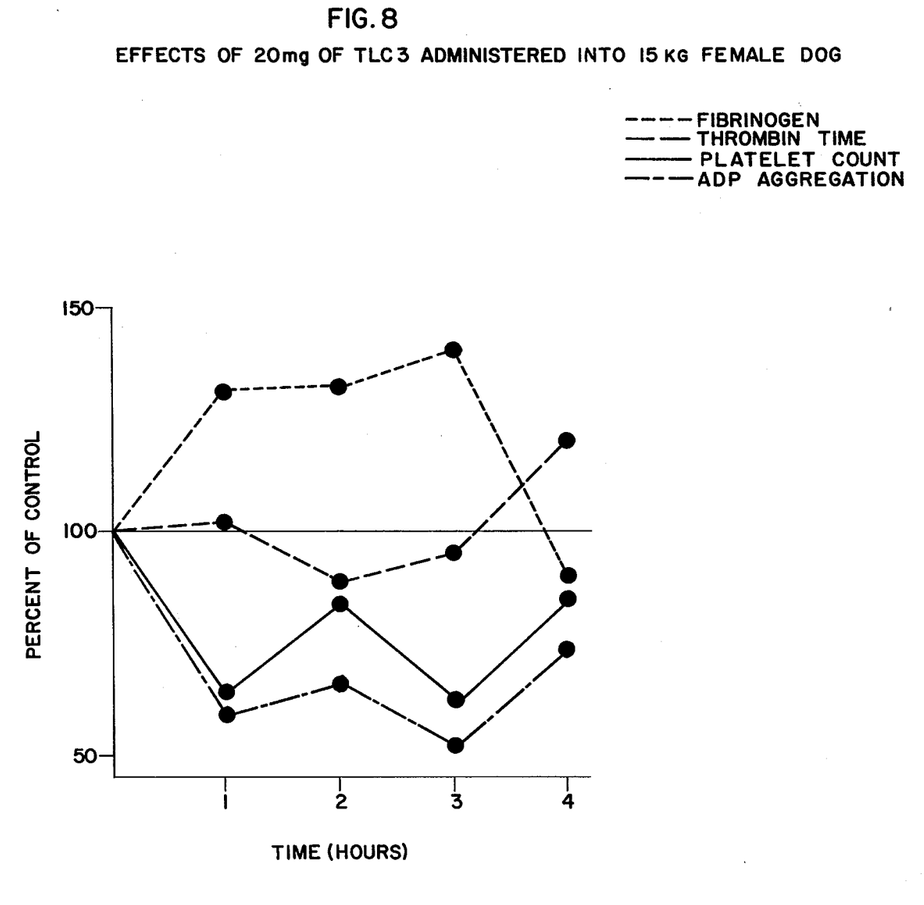

FIG. 8 discloses results which were obtained within one hour of an intravenous injection of 20 mgs of TLC 3 into a 15 kg female dog. A substantial inhibition of ADP induced platelet aggregation (60%) occured and remained during a four hour test. Further, the decreased platelet count and inhibition of ADP induced platelet aggregation appeared to parallel each other.

Two male dogs each weighing approximately 15 kgs were administered an intraperitonial injection of 30 mgs of TLC 3. Blood was drawn from the dogs just before injection and twenty four hours after injection. The platelet counts, hematocrit, thrombin time, fibrinogen and % ADP aggregation, are shown in Table II.

TABLE II

|  | Platelet Count/CC | % Hematocrit | Thrombin Time | Fibrinogen (relative) | % ADP Aggregation |
|---|---|---|---|---|---|
| DOG I | | | | | |
| Before inj. | 200,000 | 42 | 14.5 | 3.5 | 61 |
| After inj. | 150,000 | 35 | 13.0 | 6.0 | 42 |
| % change | −25 | −16 | −10.3 | +66 | −31 |
| DOG II | | | | | |
| Before inj. | 254,000 | 33 | 13 | 5.8 | 47 |
| After inj. | 78,000 | 33 | .25 | 3.4 | 32 |
| % change | −70 | 0 | +92 | −41 | −32 |

It can be seen that the response varies quite considerably from animal to animal. However, it should be noted that in each instance the response of the animals PRP to ADP was inhibited by at least 30% 24 post hours dosing. Dog 2 showed a much greater change in platelet count and thrombin time than Dog 1. It is interesting to note that even though the platelet count and ADP induced platelet aggregation in Dog 1 decreased, the plasma fibrinogen concentration increased.

Figure 9:
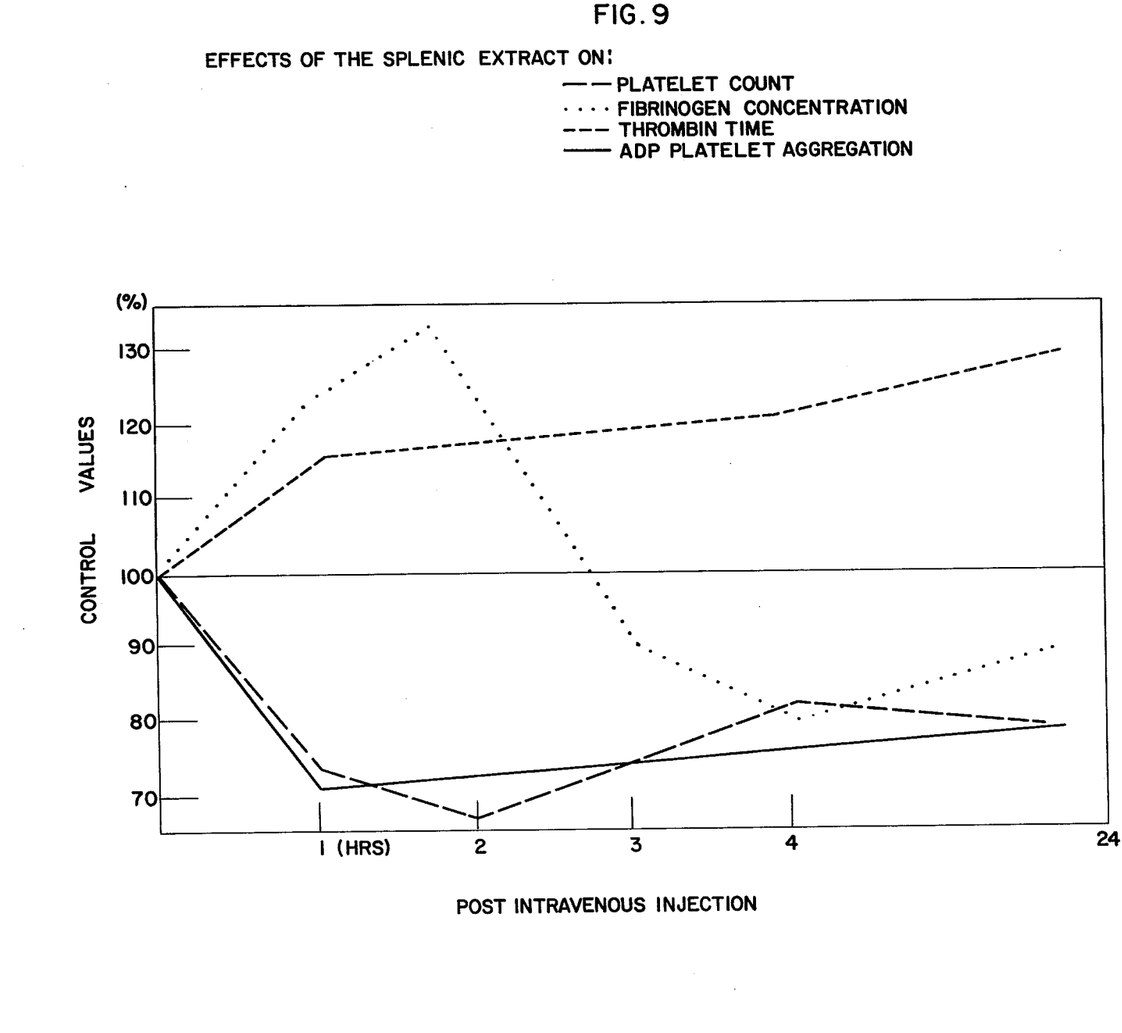

FIG. 9 shows the changes in four parameters used to quantitate blood coagulation. Within three hours of a 2 mg/kg i.v. injection of TLC 2 into 18 mongrel dogs, the appearance of a hypocoaguable state appears. ADP induced platelet aggregation is inhibited to 75% of the control values with a similar reduction in platelet count. After an initial rise in the fibrinogen concentration, this quantity decreases below the control value after three hours. Thrombin times increase after the administration of this extract. After 24 hours, the animals are still in a hypocoaguable state.

BACTERIA TEST

The administration of bacterial endotoxins into animals to produce intravascular coagulation as one of its manifestations is well known. Thus, in the event that disseminated intravascular coagulation (DIC) can be prevented or reduced, the animals chance of survival is increased. Accordingly, a lethal dose, 0.10 mgs of Difco Laboratories E, coli ones 0111:B4 Lipopolysaccharide B was injected intraperitonially into 20 outbred Swiss white mice, each weighing approximately 20 grams. Ten mice were injected with 0.2 mgs of TLC 1 or TLC 3 and the 10 remaining mice with saline three hours prior to the aforesaid lethal dose. Within two days, 9 of the mice injected with the extracts were still alive whereas 9 out of the 10 unprotected mice with the saline controls died.

Figure 10:
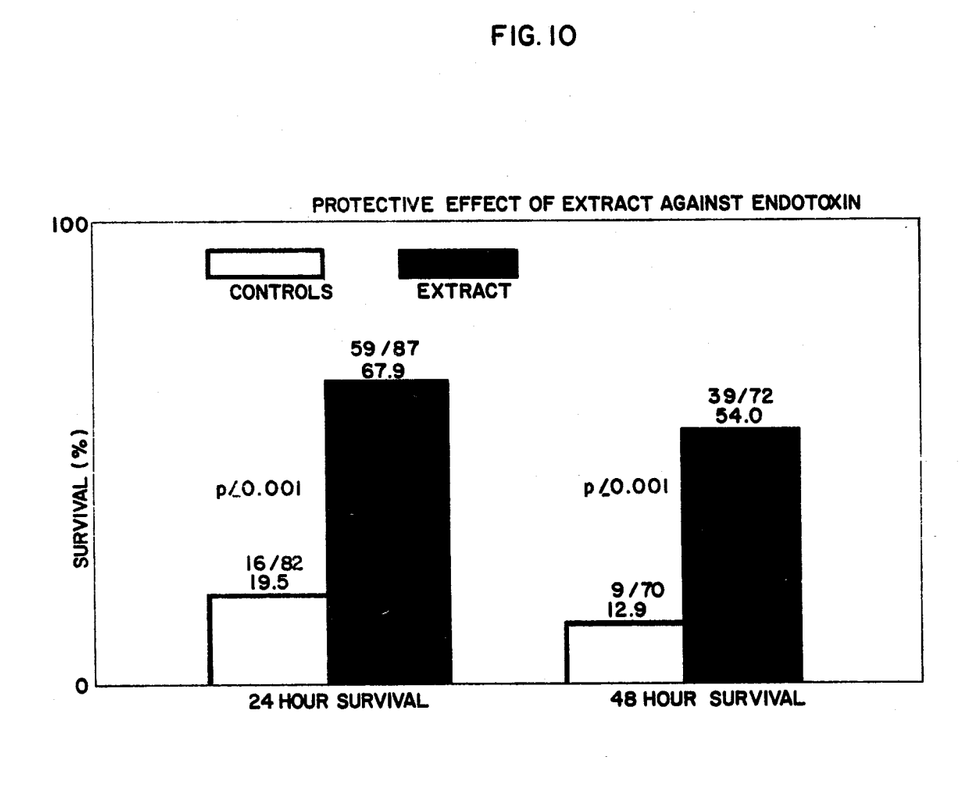

The protective effects of TLC 2 against endotoxin can be seen in FIG. 10. The data represents the cummulative results of 12 experiments employing different batches of cannine spleens and shipments of mice. The control mice had survivals of 20% and 13% at 24 and 48 hours post endotoxin administration respectively, whereas 68% and 54% survival with mice receiving about 10 mg/kg of extract three hours before the endotoxin. Mice injected simultaneously with extract and endotoxin show a 38% survival at 24 hours post dosing.

Accordingly, it can be seen that these fractions have the ability to protect mice from the lethal effects of a bacterial endotoxin by inhibiting platelet function, thereby preventing a disseminated intravascular coagulation.

Figure 11:
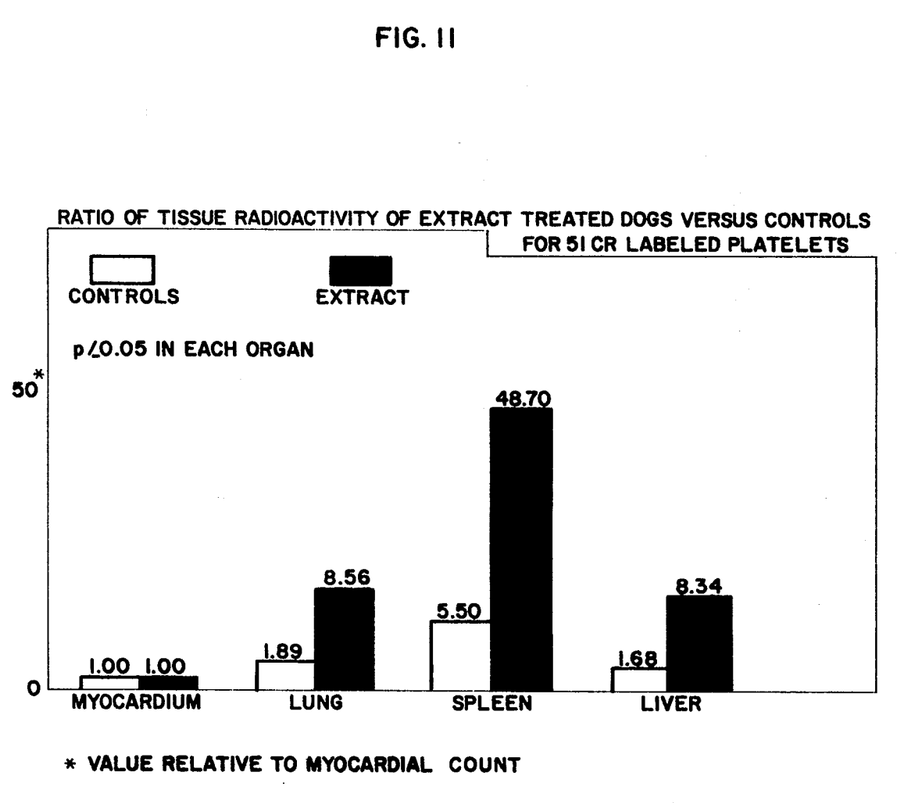

PLATELET TAGGING EXPERIMENTS $^{51}$Cr labeled autologous platelets (method of Jandl) were administered to each of seven dogs, three of which received one hour later 2 mg/kg TLC 2, and four (controls) received no treatment. The platelet counts of the extract recipients were monitored at one-half hour intervals and the animals sacrified when two consecutive platelet counts were 20% below control levels (3 hours). Controls were sacrified at three hous. Tissue radioactivity counts (CPM/gm) of various organs were obtained and calculated as ratio to myocardial tissue radioactivity. The results are shown in FIG. 11.

There were no changes for myocardial tissue or kidney, but significant changes occured in organs in organs rich in reticuloendothelial tissue. Four and one-half times more platelets were entrapped in the lungs, 8.9 times more in the spleen and 5.0 times more in the liver for dogs receiving this extract relative to the controls. This apparent stimulation of the reticuloendothelial system in dogs receiving this extract may also in part explain the survival of the extract recipient mice in endotoxin shock. Reichard S.(J. Reticuloendothel. Soc. 12, 654 (1972)) observed that stimulation of the reticuloendothelial system increased survival to traumatic and endotoxin shock. Conversely, he found that suppression of the phagocytic function of the reticuloendothelial system elimated this acquired resistance against shock.

Tolerance to endotoxin can be induced by injecting one or several sublethal doses of endotoxin before challenge by lethal dose. During this state of tolerance to endotoxin, the reticuloendothelial system is stimulated as measured by the increased rate of clearance of baceteria, carbon particles or labeled endotoxin for the blood. Furthermore, tolerance can be abolished by reticuloendothelial blockade.

TOXICITY

Rabbits and guinea pigs have been injected weekly for periods up to one year with the fractions of this invention and show no apparent histopathological, hematological or physiologically toxic effects to tissues or bone marrow.

In acute toxicity experiments, mice have been injected with single dosages of fractions of 1.0 gram per kilogram of body weight with no deaths.

THE ACTIVE EXTRACTS

The extraction procedure, followed by thin layer chromatography (isolation of particular $R_f$ values under controlled solvent and absorbant conditions) is the best means of obtaining the desired materials. Occasionally, the materials isolated after thin-layer chromatography are subjected to solubility separations (fractional crystallization) whereby the more acetone soluble materials show a greater biological activity than the less acetone solubles.

At present the most reliable methods for testing the effects of these extracts on platelet function are the increase in survival from the lethality of bacterial endotoxin (E. Coli) in mice and the inhibition of ADP induced platelet aggregation in human platelet rich plasmas (PRP.)

As described previously, Swiss white mice were injected intraperitoneally with TLC 1, TLC 2 and TLC 3 (3-15 mg/kg b.w.) or saline (0.1cc) three hours before the administration of E. Coli endotoxin (0.1 mg/mouse). The greater the percent survival for a constant dose of extract, the greater the quantity of active material administered. Similarly, one would expect fractions which inhibit ADP induced platelet aggregation to the greatest extent for a particular concentration, to have the largest quantity of active principle within its composition.

PLATELET RAISING FRACTIONS

While reference has been made to the inventive fractions possessing the capability of increasing platelet count, upon its decomposition during storage, a method has been devised for recovering platelet raising fractions from the spleen.

A method similar to that described in Example II is employed to a point where the splenic materials are removed from the acetone. To this mixture of splenic materials was added 2 liters of benzene. The mixture was heated for 18 hours 50° C, filtered and the benzene evaporated off. Upon a thin layer chromatography of the resultant mixture, a chromatogram similar to that described for the platelet reducing fraction was obtained. However, the opaque area of the recovered fraction in this procedure which was extracted from the silica, with benzene and acetone corresponded to fraction TLC 2 previously described herein, except that it produced platelet raising effects on the animals tested.

TEST EFFECTS OF PLATELET RAISING FRACTIONS

Forty milligrams of the just described solvent free platelet raising material were injected into rabbits and resulted in the elevation of platelet counts 40 percent (average 469,000 to 665,000 per C.C.) for a duration of three days. When 20 mgs were injected into two dogs, the average platelet counts doubled 230,000 to 480,000 per c.c. within one hour and remained at that level for the three hours of the experiment. Attempts to obtain blood samples for coagulation studies revealed the extreme hypercoagulability of these dog bloods. Many of the samples clotted in the collecting tubes, with anticoagulants such as citrate and oxalate.

Those samples which did not clot disclosed a 30% decrease in thrombin time, a 15% increase in plasma fibrinogen and a 30% increase in ADP induced platelet aggregation over the control values, thus producing a hypercoaguable state.

It is believed that the predominance of those platelet increasing fractions which produce a hypercoaguable state over those platelet reducing fractions which produce a hypocoaguable state, may in part be responsible for the thrombotic diseases in man, whereas, if the factors producing a hypocoaguable state become too great, then the bleeding or hemorrhagic syndromes such as purpura develop. In order for the normal coagulation functions to be maintained these fractions or fractors must balance each other.

CHARACTERIZATION OF THE ACTIVE FRACTIONS

The isolation procedures including the thin-layer chromatography are the best methods for isolating and chracterizing these bio-active fractions. The major problem in characterizing these materials is their labile nature and complexity. These isolated materials although complex in nature are chromatographically "pure" (thin-layer) and yield reproducible bioactivity. If fractions TLC 1–3 are isolated as described and then rechromatographed under identical conditions decomposition products are observed (materials with $R_f$ values other than that isolated.) If the isolated materials are kept for longer periods of time, the amount of decomposition products increases proportionally with an understandable decrease in the inhibitory effects of these materials on platelet function. If stored a sufficiently long period of time the decomposition products of these fractions can cause stimulation of platelet function (hypercoaguable state) e.g. an increase in lethality to endotoxin, and increase in ADP induced platelet aggregation, and a decrease in bleeding times.

The $R_f$ values of the active fractions are given below. The plates were used without pre-heating. Qualitatively, TLC 1 is a faster moving band with $R_f$ values of 0.6–0.7 in the solvent systems employed. TLC 2, is comprised of two or more components which for convenience are all collected together. TLC 2A is faster moving than TLC 2B. These materials have $R_f$ values between that the dyes butter yellow and sudan red in these solvent systems. TLC 3 is the material remaining at the origin.

| | $R_f$ Values × 100 | |
|---|---|---|
| | Analtech Silica Gel GF 250 Microns Thick; Solvent=Benzene | Analtech Silica Gel GF/M.H. 250 Microns Thick; Solvent=Benzene |
| TLC 1 | 66 | 60 |
| TLC 2A | 37 | 25 |
| TLC 2B | 28 | 15 |
| TLC 3 | 0 | 0 |
| Butter yellow | 40 | 28 |
| Sudan red 6 | 17 | 12 |
| Indophenol blue | 5 | 5 |

SAPONIFICATION OF ACTIVE FRACTIONS

If TLC 1–3 are saponified under mild conditions (1M KOH in methanol at room temperature) a large number of different materials are present (at least 4) in each thin-layer chromatogram (same condition as described). This enhances the concept that these bioactive materials are complex in nature.

The infrared spectra peaks of fractions TLC 1, TLC 2A, TLC 2B and TLC 3 contained in the table below. The materials were dissolved in $CHCl_3$ and pipeted on NaCl discs. The solvent was then evaporated leaving a film of the material. A Perkin Elmer model 247 was the instrument employed for obtaining the spectra. Below are the spectra in tabular form. Some peaks in TLC 1 may be that of BHT which has the same $R_f$ value as TLC 1.

| TLC 1 | TLC 2A | TLC 2B | TLC 3 |
|---|---|---|---|
| cm-1 | cm-1 | cm-1 | cm-1 |
| 3560 | 2960 | 3300 | 3250 |
| 3150 | 2900 | 2900 | 2850 |
| 2900 | 2870 | 2860 | 2780 |
| 2860 | 2800 | 2800 | 2270 |
| 2800 | 1730 | 2270 | 1705 |
| 2300 | 1450 | 1720 | 1435 |
| 1580 | 1365 | 1710 | 1355 |
| 1460 | 1230 | 1570 | 1220 |
| 1440 | 1145 | 1420 | 1140 |
| 1360 | 1105 | 1360 | 1030 |
| 1340 | 1090 | | 790 |
| 1300 | | | |
| 1230 | | | |
| 1210 | | | |
| 1140 | | | |
| 1010 | | | |
| 845 | | | |

I claim:

1. A process of extracting and isolating a material from a spleen which inhibits platelet function, which comprises:

subjecting the spleen to a polar solvent having a high dielectric constant of at least 20, and subjecting the resultant polar solvent filtrate to a silica gel thin-layer chromatograph process wherein a benzene eluting solvent is utilized for separating and recovering the desired material therefrom, said material having an $R_f$ value ranging from about 0 to 0.73.

2. A process of extracting and isolating a material, according to claim 1, wherein said resultant polar solvent filtrate is subjected to an Analtech silica gel G.F. plate.

3. A process of extracting and isolating a material from spleen which inhibits platelet function, which comprises:

subjecting the spleen to a polar solvent having a high dielectric constant of at least 20, and subjecting the resultant polar solvent filtrate to a glass column chromatography process wherein an eluting solvent from the group benzene and methanol is employed for separating and recovering the desired material therefrom, said material having an $R_f$ value ranging from about 0 to 0.73, when subjected to an Analtech silica gel G.F. plate.

4. A process of extracting and isolating a material, according to claim 3, wherein the said resultant polar filtrate is subjected to silicic acid.

5. A material for inhibiting platelet function, lowering animal platelet counts or fibrinogen concentration, or both, derived from a process of extracting and isolating said material from a spleen, which comprises:

subjecting the spleen to a polar solvent having a high dielectric constant of at least 20, and subjecting the resultant polar solvent filtrate to a silica gel thin-layer chromatography process wherein a benzene eluting solvent is utilized for separating and recovering the desired material therefrom, said material having an $R_f$ value ranging from about 0 to 0.73 and a melting point not in excess of 70° C.

6. A material, according to claim 5, wherein said resultant polar solvent is subjected to an Analtech silica gel G.F. plate.

7. A material for inhibiting platelet function, lowering animal platelet counts or fibrinogen concentration, or both, derived from a process of extracting and isolating said material from a spleen, which comprises;

subjecting the spleen to a polar solvent having a high dielectric constant of at least 20, and subjecting the resultant polar solvent filtrate to a glass column chromatography process wherein an eluting solvent from the group benzene and methanol is employed for separating and recovering the desired material therefrom, said material having an $R_f$ value ranging from about 0 to 0.73, when subjected to an Analtech silica get G.F. plate.

8. A material, according to claim 7, wherein the said resultant polar filtrate is subjected to silicic acid.

9. A lipid material for inhibiting platelet function derived from an animal spleen and having a melting point not in excess of 70° C; said material being extractable by and soluble in acetone, benzene and ether; said material and the dyes butter yellow, sudan red 6 and indophenol blue, when subjected to a 250 micron thick Analtech silica gel G.F. plate employing a benzene eluting solvent, yielding an $R_f$ value of 0.66 for said material and $R_f$ values of 0.40, 0.17 and 0.05 for the dyes butter yellow, sudan red 6 and indophenol blue, respectively; and, said material further depicting at least one of the peaks on an infra red spectra whose wavelengths in $cm^{-1}$ include 3560, 3150, 2900, 2860, 2800, 2300, 1580, 1460, 1440, 1360, 1340, 1300, 1230, 1210, 1140, 1010 and 845.

10. A lipid material for inhibiting platelet function derived from an animal spleen and having a melting point not in excess of 70° C; said material being extractable by and soluble in acetone, benzene and ether; said material and the dyes butter yellow, sudan red 6 and indophenol blue, when subjected to a 250 micron thick Analtech silica gel G.F. plate employing a benzene eluting solvent, yielding an $R_f$ value of .37 for said material and $R_f$ values of 0.40, 0.17 and 0.05 for the dyes butter yellow, sudan red 6 and indophenol blue, respectively; and, said material further depicting at least one of the peaks on an infra red spectra whose wavelengths in $cm^{-1}$ include 2960, 2900, 2870, 2800, 1730, 1450, 1365, 1230, 1145, 1105 and 1090.

11. A lipid material for inhibiting platelet function derived from an animal spleen and having a melting point not in excess of 70° C; said material being extractable by and soluble in acetone, benzene and ether; said material and the dyes butter yellow, sudan red 6 and indophenol blue, when subjected to a 250 micron thick Analtech silica gel G.F. plate employing a benzene eluting solvent, yielding an $R_f$ value of .28 for said material and $R_f$ values of 0.40, 0.17 and 0.05 for the dyes butter yellow, sudan red 6 and indophenol blue, respectively; and, said material further depicting at least one of the peaks on an infra red spectra whose wavelengths in $cm^{-1}$ include 3300, 2900, 2860, 2800, 2270, 1720, 1710, 1570, 1420 and 1360.

12. A lipid material for inhibiting platelet function derived from an animal spleen and having a melting point not in excess of 70° C; said material being extractable by and soluble in acetone, benzene and ether; said material and the dyes butter yellow, sudan red 6 and indophenol blue, when subjected to a 250 micron thick Analtech silica gel G.F. plate employing a benzene eluting solvent, yielding an $R_f$ value of 0 for said material and $R_f$ values of 0.40, 0.17 and 0.05 for the dyes yellow, sudan red 6 and indophenol blue, respectively; and, said material further depicting at least one of the peaks on an infra red spectra whose wave-lenghts in $cm^{-1}$ include 3250, 2850, 2850, 2780, 2270, 1705, 1435, 1355, 1220, 1140, 1030 and 790.

* * * * *